United States Patent
Kiesele et al.

[11] Patent Number: 5,997,706
[45] Date of Patent: Dec. 7, 1999

[54] ELECTROCHEMICAL MEASURING CELL FOR DETECTING ARSINE AND PHOSPHINE

[75] Inventors: Herbert Kiesele; Frank Mett, both of Lübeck, Germany

[73] Assignee: Dräger Sicherheitstechnik GmbH, Germany

[21] Appl. No.: 09/057,638

[22] Filed: Apr. 9, 1998

[30] Foreign Application Priority Data

Oct. 15, 1997 [DE] Germany .......................... 197 45 486

[51] Int. Cl.[6] ................................................ G01N 27/404
[52] U.S. Cl. ........................................... 204/415; 205/775
[58] Field of Search .................... 204/415, 431, 204/432; 205/775, 782.5, 783

[56] References Cited

U.S. PATENT DOCUMENTS

| | | |
|---|---|---|
| 3,622,488 | 11/1971 | Chand et al. .......................... 204/415 |
| 3,668,101 | 6/1972 | Bergman .................................. 204/415 |
| 3,756,923 | 9/1973 | Dahms .................................... 204/415 |
| 4,406,770 | 9/1983 | Chan et al. ............................. 204/431 |
| 5,128,018 | 7/1992 | Kiesele ................................... 204/415 |

*Primary Examiner*—T. Tung
*Attorney, Agent, or Firm*—McGlew and Tuttle, P.C.

[57] ABSTRACT

An electrochemical measuring cell for detecting arsine and phosphine, containing at least one working electrode (3) consisting of a catalytically inactive material and a reference electrode (4) in an electrolyte space (6), which is filled with an aqueous electrolyte (9) and is sealed with a gas-permeable membrane (2) toward the gas to be detected, shall be improved in terms of the cross sensitivity to other gases. To accomplish this object, the working electrode (3) is designed as a thin-layer electrode and the electrolyte (9) consists of sulfuric acid with an electrolyte additive consisting of silver sulfate.

10 Claims, 1 Drawing Sheet

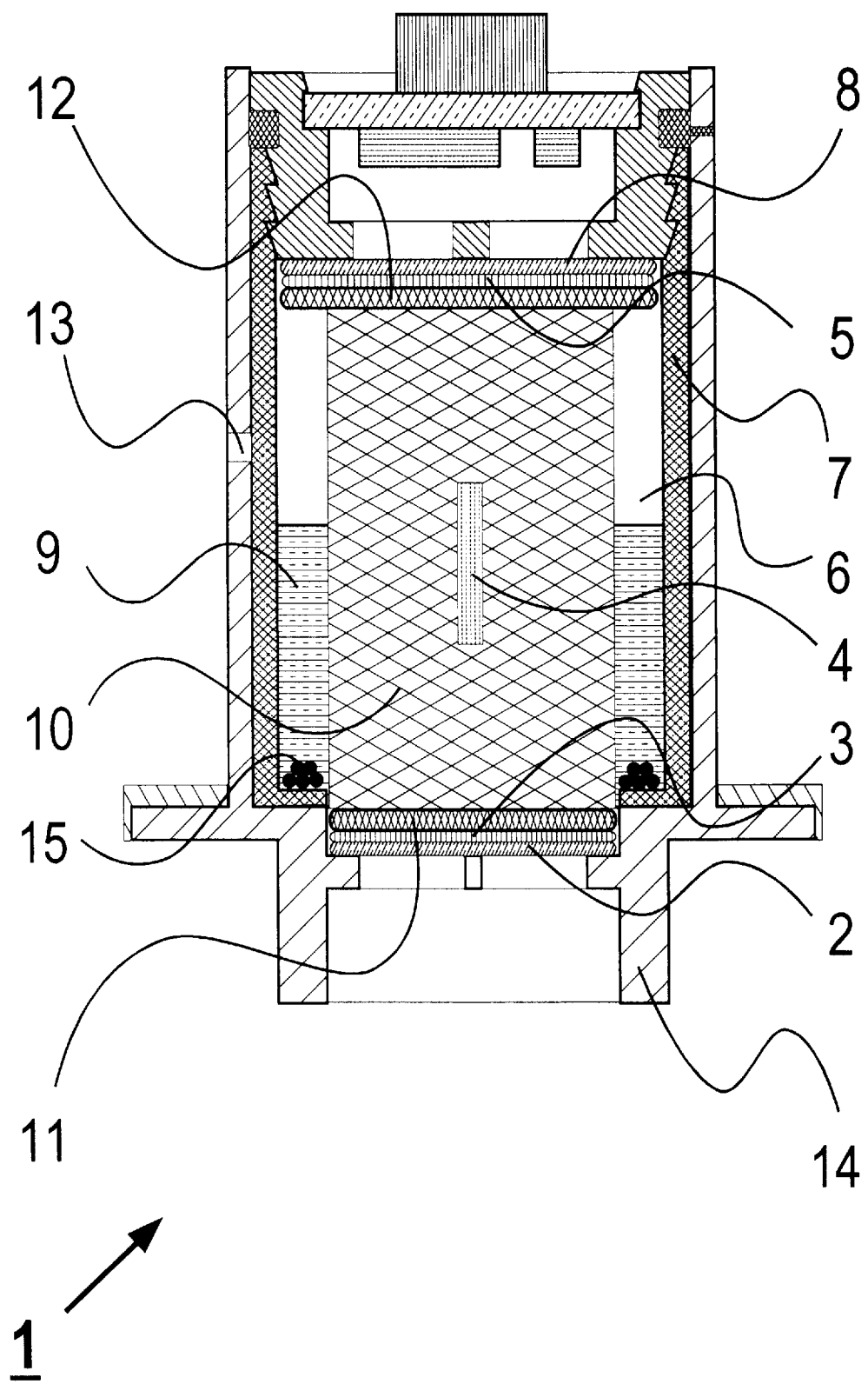

ELECTROCHEMICAL MEASURING CELL FOR DETECTING ARSINE AND PHOSPHINE

FIELD OF THE INVENTION

The present invention pertains to an electrochemical measuring cell for detecting arsine and phosphine, containing at least one working electrode consisting of a catalytically inactive material and a reference electrode in an electrolyte space, which is filled with an aqueous electrolyte and is sealed with a gas-permeable membrane toward the gas to be detected.

BACKGROUND OF THE INVENTION

An electrochemical measuring cell for detecting hydride gases, especially phosphine and arsine, has become known from EP 436 148 B1. In the prior-art measuring cell, a working electrode, a reference electrode, and an auxiliary electrode are arranged in an electrolyte space of a measuring cell. The electrolyte space is sealed by means of a gas-permeable membrane toward the environment, which contains the gas sample to be measured, which contains the hydride gas to be detected. Sulfuric acid with catalytic additives is used as the electrolyte.

Even though the prior-art measuring cell is characterized by high sensitivity, there are cross sensitivities to a number of other gases. These cross sensitivities are especially disturbing in the case of certain applications, or they may lead to false alarms. Thus, the prior-art measuring cell also responds to $NO_2$, $H_2$, $C_2H_2$, $SO_2$, $H_2O_2$, and $O_3$, besides phosphine and arsine.

SUMMARY AND OBJECTS OF THE INVENTION

The primary object of the present invention is to improve an electrochemical measuring cell of the above-described type in terms of the cross sensitivity to other gases.

According to the invention, an electrochemical measuring cell for detecting arsine and phosphine is provided, containing at least one working electrode comprising a catalytically inactive material and a reference electrode. The electrodes are disposed in an electrolyte space, which is filled with an aqueous electrolyte and is sealed with a gas-permeable membrane toward the gas to be detected. The working electrode is provided as a thin-layer electrode, and sulfuric acid is provided as the electrolyte which also contains an electrolyte additive consisting of silver sulfate.

According to another aspect of the invention, an electrochemical measuring cell for detecting arsine and phosphine is provided containing at least one working electrode, comprising a catalytically inactive material and a reference electrode. The electrodes are disposed in an electrolyte space which is filled with an aqueous electrolyte and is sealed toward the gas to be detected with a gas-permeable membrane. The electrolyte is phosphoric acid, to which an electrolyte additive consisting of silver phosphate is added.

The advantage of the present invention is the surprisingly found fact that the selectivity of the detection of arsine and phosphine is markedly improved compared with other gases e.g., $H_2$, $C_2H_2$, and $NO_2$, by the combination of a working electrode designed as a thin layer with an electrolyte that consists of sulfuric acid and to which an electrolyte additive consisting of silver sulfate is added. As an alternative to sulfuric acid, it is also possible to use as the electrolyte phosphoric acid, which contains silver phosphate as the electrolyte additive.

The electrochemical reaction within the measuring cell takes place such that the phosphine or arsine to be detected reacts selectively with the electrolyte additive within the electrolyte space and the reaction product is then detected at the working electrode. By using a thin-layer electrode as the working electrode, the catalytic activity of the working electrode is low with respect to other gas components of the gas sample to be measured because of its small surface. Therefore, only a comparatively weak measured signal is generated by the other gas components of the gas sample to be measured at the working electrode. An electrochemical measuring cell containing sulfuric acid as the electrolyte and silver sulfate as the electrolyte additive is characterized by high sensitivity and a short response time in the case of the detection of arsine and phosphine.

The measuring cell according to the present invention may be designed as a two-electrode measuring cell or as a three-electrode measuring cell with an additional auxiliary electrode. The measuring electrodes are connected to a potentiostat in the known manner as a detection device.

It is especially advantageous to add the electrolyte additive in a saturated solution to the electrolyte. Measuring cells of such a design have an especially high long-term stability. A saturated solution of the electrolyte additive can be advantageously obtained by the electrolyte additive being present as an excess solute in the electrolyte space. A spent electrolyte additive can thus be continuously replaced from the excess solute.

Gold is especially suitable as a material for the working electrode, because it can be processed in a simple manner in terms of the manufacturing technique and is electrochemically compatible with the electrolyte proposed according to the present invention. Experiments have shown that especially selective measured signals are obtained with a working electrode made of gold.

The reference electrode and the auxiliary electrode may consist of gold or also of another material, without any measurable reduction in the selectivity or sensitivity.

Suitable layer thicknesses of the working electrode are obtained if it is sputtered or vapor deposited to the diffusion membrane. Advantageous layer thicknesses are between 50 nm and 500 nm.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

The only FIGURE is a cross sectional view of an electrochemical measuring cell according to the invention.

DESCRIPTION OF THE PREFERRED EMBODIMENT

Referring to the drawing in particular, the only FIGURE shows an electrochemical measuring cell 1 with a working electrode 3 consisting of gold, which is sputtered to a porous PTFE membrane 2, a reference electrode 4 consisting of gold powder, and an auxiliary electrode 5, which likewise consists of gold and is introduced into an electrolyte space 6 of a measuring cell housing 7. A porous PTFE support membrane 8 is used as the electrode carrier for the auxiliary electrode 5. The electrolyte 9 is 4-M sulfuric acid with silver sulfate in a saturated solution as an additive, wherein the saturated solution is stabilized by means of an excess solute 15 of silver sulfate. Spent silver sulfate can thus be continuously replaced from the excess solute 15. The electrolyte 9 is accommodated within the electrolyte space 6 by a porous glass body 10, which contains the reference electrode 4 in its middle and establishes the electrolytic connection between the electrodes 3, 5 by means of two mats 11, 12. The measuring cell housing 7 consists of porous PTFE to establish a pressure equalization between the electrolyte space 6 and the environment via the openings 13. The electrodes 3, 4, 5 are connected to a potentiostat, not shown in the figure, in the known manner. The gas sample containing the phosphine or arsine to be analyzed reaches the working electrode 3 via the connection 14 by diffusion through the membrane 2.

The arrangement of the figure can also be used with the electrolyte 9 being phosphoric acid, to which an electrolyte additive consisting of silver phosphate is added. In this arrangement the electrochemical measuring cell 1 with the working electrode 3 consisting of gold, which is sputtered to the porous PTFE membrane 2, the reference electrode 4 consisting of gold powder, and an auxiliary electrode 5, which likewise consists of gold is again used and is introduced into an electrolyte space 6 of a measuring cell housing 7. The porous PTFE support membrane 8 is again employed as the electrode carrier for the auxiliary electrode 5. However, the electrolyte 9 is phosphoric acid, to which an electrolyte additive consisting of silver phosphate is added.

The electrolyte 9 (phosphoric acid, to which an electrolyte additive consisting of silver phosphate is added) is accommodated within the electrolyte space 6 by the porous glass body 10, which contains the reference electrode 4 in its middle and establishes the electrolytic connection between the electrodes 3, 5 by means of the two mats 11, 12. The measuring cell housing 7 consists of porous PTFE to establish a pressure equalization between the electrolyte space 6 and the environment via the openings 13. The electrodes 3, 4, 5 are connected to a potentiostat, not shown in the figure, in the known manner. The gas sample containing the phosphine or arsine to be analyzed reaches the working electrode 3 via the connection 14 by diffusion through the membrane 2.

While specific embodiments of the invention have been shown and described in detail to illustrate the application of the principles of the invention, it will be understood that the invention may be embodied otherwise without departing from such principles.

What is claimed is:

1. An electrochemical measuring cell for detecting arsine and phosphine comprising at least one working electrode formed of gold;

a reference electrode in an electrolyte space, said electrolyte space being filled with an aqueous electrolyte and being sealed with a gas-permeable membrane toward the gas to be detected, said working electrode being a thin-layer electrode of less than 500 nm on said gas-permeable membrane, and said electrolyte being sulfuric acid and containing silver sulfate as an electrolyte additive.

2. The electrochemical measuring cell in accordance with claim 1, wherein said electrolyte additive is present in said electrolyte in a saturated solution.

3. The electrochemical measuring cell in accordance with claim 1, wherein excess solute consisting of the electrolyte additive is present in said electrolyte space.

4. The electrochemical measuring cell in accordance with claim 1, wherein said working electrode is prepared as a sputtered electrode using a sputtering process.

5. The electrochemical measuring cell in accordance with claim 1, wherein said working electrode is applied to said gas-permeable membrane by vapor deposition.

6. An electrochemical measuring cell for detecting arsine and phosphine, comprising:

at least one working electrode formed of gold;

a reference electrode in an electrolyte space, said electrolyte space being filled with an aqueous electrolyte and being sealed with a gas-permeable membrane toward the gas to be detected, said working electrode being a thin-layer electrode of less than 500 nm on said gas-permeable membrane, said electrolyte being phosphoric acid, to which an electrolyte additive consisting of silver phosphate is added.

7. The electrochemical measuring cell in accordance with claim 6, wherein said electrolyte additive is present in said electrolyte in a saturated solution.

8. The electrochemical measuring cell in accordance with claim 6, wherein excess solute consisting of the electrolyte additive is present in said electrolyte space.

9. The electrochemical measuring cell in accordance with claim 6, wherein said working electrode is prepared as a sputtered electrode using a sputtering process.

10. The electrochemical measuring cell in accordance with claim 6, wherein said working electrode is applied to said gas-permeable membrane by vapor deposition.

* * * * *